United States Patent
Vaia et al.

(10) Patent No.: US 10,758,983 B1
(45) Date of Patent: Sep. 1, 2020

(54) CONCENTRATED SYNTHESIS OF MONODISPERSED GOLD NANORODS

(71) Applicant: Government of the United States, as represented by the Secretary of the Air Force, Wright-Patterson AFB, OH (US)

(72) Inventors: Richard A. Vaia, Beavercreek, OH (US); Kyoungweon Park, Beavercreek, OH (US)

(*) Notice: Subject to any disclaimer, the term of this patent is extended or adjusted under 35 U.S.C. 154(b) by 350 days.

(21) Appl. No.: 15/954,646

(22) Filed: Apr. 17, 2018

(51) Int. Cl.
*B22F 9/24* (2006.01)
*B22F 1/00* (2006.01)
*C22B 3/00* (2006.01)
*B82Y 30/00* (2011.01)
*B82Y 40/00* (2011.01)

(52) U.S. Cl.
CPC ............ *B22F 9/24* (2013.01); *B22F 1/0018* (2013.01); *C22B 11/04* (2013.01); *B22F 2301/255* (2013.01); *B82Y 30/00* (2013.01); *B82Y 40/00* (2013.01); *Y10S 977/762* (2013.01); *Y10S 977/81* (2013.01); *Y10S 977/896* (2013.01)

(58) Field of Classification Search
CPC .......... B22F 9/24; B22F 1/0018; C22B 11/04; B82Y 30/00; B82Y 40/00; Y10S 977/762; Y10S 977/896
See application file for complete search history.

(56) References Cited

U.S. PATENT DOCUMENTS 7,588,624 B2   9/2009 Mirkin et al.
9,314,849 B2 * 4/2016 Tracy .................. B22F 9/24
(Continued)

FOREIGN PATENT DOCUMENTS

CN   102367589 A   3/2012
CN   103934467 A   7/2014
(Continued)

OTHER PUBLICATIONS

Babk Nikoobakht and Mostafa A. El-Sayed, Preparation and Growth Mechanism of Gold Nanorods (NRs) Using Seed-Mediated Growth Method, Chemistry of Materials Article pubs.asc.org/cm, U.S.A., 2003.
(Continued)

*Primary Examiner* — Christopher S Kessler
*Assistant Examiner* — Jiangtian Xu
(74) *Attorney, Agent, or Firm* — AFMCLO/JAZ; Timothy M. Barlow

(57) ABSTRACT

A method for synthesizing nanostructures includes introducing a solution of seed crystals into an initial growth solution to form a nanostructure synthesis mixture. The initial growth solution includes a precursor material and a reducing agent in a surfactant solution. Growth of nanostructures in the nanostructure synthesis mixture is monitored during a period of anisotropic growth of the nanostructures to determine a shift from stage II growth of the nanostructures to stage III growth of the nanostructures. The shift from stage II growth to stage III growth is identified, and after identifying the shift, a second growth solution is added to the nanostructure synthesis mixture coincident in time with the shift. The second growth solution includes the precursor material and the reducing agent in the surfactant solution.

19 Claims, 4 Drawing Sheets

(56) References Cited

U.S. PATENT DOCUMENTS

| | | | |
|---|---|---|---|
| 9,375,790 | B2 | 6/2016 | Murphy et al. |
| 9,395,372 | B2 | 7/2016 | Hoonacker et al. |
| 9,678,066 | B2 | 6/2017 | Roskamp et al. |
| 2011/0189483 | A1 | 8/2011 | Zubarev et al. |

FOREIGN PATENT DOCUMENTS

| | | |
|---|---|---|
| CN | 103132143 B | 4/2015 |
| CN | 105413712 A | 3/2016 |
| CN | 103934466 B | 3/2017 |
| CN | 104985178 B | 5/2017 |
| CN | 106984830 A | 7/2017 |
| CN | 107008895 A | 8/2017 |
| WO | 2017004301 A1 | 1/2017 |

OTHER PUBLICATIONS

Kristina L. Tran, Synthesis, Characterization, and Self-Assembly of Gold Nanorods and Nanoprisms, University of South Florida, U.S.A., Scholar Commons, Jun. 29, 2010.

Kyoungweon Park, Lawrence F. Drummy, Robert C. Wadems, Hilmar Koerner, Dhrita Nepal, Laura Fabris, and Richard A. Vaia, Growth Mechanism of Gold Nanorods, Chemistry of Materials Article pubs.asc.org/cm, U.S.A., 2012.

Leonardo Scarabelli, Ana Sanchez-Iglesias, Jorge Perez-Juste, Luis M. Liz-Marzan, A "Tips and Tricks" Practical Guide to the Synthesis of Gold Nanorods, The Journal of Physical Chemistry Letters, pubs.asc.org/JPCL, Spain, Published Nov. 5, 2015.

Leonid Vigderman and Eugene R. Zubarev, High-Yield Synthesis of Gold Nanorods with Longitudial SPR Peak Greater than 1200 nm Using Hydroquinone as a Reducing Agent, Chemistry of Materials Article, pubs.asc.org/cm, Department of Chemistry, Rice University, Houston, Texas U.S.A, 2013.

Seong S. Seo, Xiaohong Wang, Davoy Murray, Direct Monitoring of Gold Nanorod Growth, Department of Naturual Sciences, Albany State University, Albany, Georgia U.S.A., Ionics 2009.

Yingying Wang, Saran Long, Silvije Vdovic, and Xuefei Wang, Fine Tuning of the Longitudinal Plasmon Resonance of Gold Nanorods by Depleting Gold Precursor, Chemistry of Materials Article, pubs. asc.org/cm, Beijing National Laboratory for Molecular Sciences, Institute of Chemistry, Chinese Academy of Sciences, Beijing, China, 2012.

\* cited by examiner

[xS /yG₁+zG₂ GROWTH]

SEED SOLUTION S
- Au-PRECURSOR
- SURFACTANT
- STRONG REDUCING AGENT
- SOLVENT

AGE SEEDS, ADD xS VOL OF SEED SOLUTION TO FIRST GROWTH SOLUTION G₁

FIRST GROWTH SOLUTION = y G₁
- Au-PRECURSOR
- ADDITIVES
- SURFACTANT
- MILD REDUCING AGENT
- SOLVENT

END STAGE II, ADD SECOND GROWTH SOLUTION G₂

SECOND GROWTH SOLUTION = z G₂
- Au-PRECURSOR
- ADDITIVES
- SURFACTANT
- MILD REDUCING AGENT
- SOLVENT

1S/1G₁ UP TO 100S/100G₁, AFTER STAGE II, FOLLOWED BY ADDITION OF 1G₂ UP TO 100 G₂

[10S /1G₁+10G₂ GROWTH]

SEED SOLUTION S
- 0.0025 mL OF 0.1 M HAuCl₄
- 364mg OF CTAB
- 0.6 mL OF 0.01 M NaBH₄
- 10 mL OF H₂O

AGE 5min, ADD 0.01mL OF 5min AGED SEEDS = 10 S

FIRST GROWTH SOLUTION = 1G₁
- 0.050 mL OF 0.1M HAuCl₄
- 0.008 mL OF 0.1M AgNO₃
- 364 mg OF CTAB
- 0.053 mL of 0.1 M ASCORBIC ACID
- 10 mL OF H₂O

END STAGE II, ADD SECOND GROWTH SOLUTION

SECOND GROWTH SOLUTION = 10G₂
- 0.5 mL OF 0.1 HAuCl₄
- 0.08 mL OF 0.1M AgNO₃
- 364 mg OF CTAB
- 0.53 mL of 0.1 M ASCORBIC ACID
- 10 mL OF H₂O

FIG. 1

CONCENTRATED SYNTHESIS OF MONODISPERSED GOLD NANORODS

GOVERNMENT INTEREST

The invention described herein may be manufactured and used by or for the Government of the United States for all governmental purposes without the payment of any royalty.

CROSS REFERENCE TO RELATED APPLICATIONS

None.

FIELD OF THE INVENTION

This invention relates to the field of synthesis of nanostructures. More particularly, this invention relates to methods for synthesizing nanostructures, such as gold nanorods.

BACKGROUND OF THE INVENTION

Improvement is desired in the synthesis of nanostructures, and in particular of gold nanorods. Conventional processes have numerous shortcomings which result in high costs of produced nanostructures. What is desired is an improved process that can reduce the costs of the produced nanostructures as well as facilitating the synthesis of nanostructures.

The invention advantageously provides methods for the synthesis of nanostructures that offers enhanced growth rates as compared to conventional methods. In particular, methods according to the disclosure advantageously enable enhanced synthesis of nanostructures, characterized by substantially increased growth rates of nanostructures resulting from targeted addition of concentrated growth solution after identifying the shift from stage II growth to stage III growth. The increased growth rates provide increased yield of nanostructures, which is advantageous to reduce costs of the production of nanostructures.

SUMMARY OF THE INVENTION

The above and other needs are met by the disclosed methods for synthesizing nanostructures.

In one aspect, the method includes introducing a solution of seed crystals into an initial growth solution to form a nanostructure synthesis mixture. The initial growth solution includes a precursor material and a reducing agent in a surfactant solution. Growth of nanostructures in the nanostructure synthesis mixture is monitored during a period of anisotropic growth of the nanostructures to determine a shift from stage II growth of the nanostructures to stage III growth of the nanostructures. The shift from stage II growth to stage III growth is identified, and after identifying the shift, a second growth solution is added to the nanostructure synthesis mixture coincident in time with the shift. The second growth solution includes the precursor material and the reducing agent in the surfactant solution.

A variety of options may be employed for this aspect. The step of monitoring the growth of the nanostructures may comprise spectroscopic monitoring, and the nanostructures may comprise nanorods. The seed crystals may comprise gold seed crystals, and the surfactant solution may have a concentration of from about 0.05 M to about 0.2 M. The surfactant solution may comprise a cetyl trimethyl ammonium surfactant solution or any other quarternary ammonium bromide surfactant, or a combination of a quaternary ammonium bromide surfactant and a quaternary ammonium halide surfactant. Also, the step of monitoring the growth of the nanostructures may comprise spectroscopic monitoring, and the determination of a shift from stage II growth of the nanostructures to stage III growth of the nanostructures may comprise determining a period of anisotropic growth characterized by a cessation of a red shift in a longitudinal surface plasmon resonance absorbance spectrum or a beginning of a blue shift in the longitudinal surface plasmon resonance absorbance spectrum.

In another aspect, the method relates to synthesizing gold nanorods, and includes the steps of introducing gold seed crystals into an initial growth solution to form a gold nanorod synthesis mixture. The initial growth solution includes an initial gold precursor and a reducing agent in an initial surfactant solution provided by a cetyl trimethyl ammonium surfactant having a concentration range of about 0.05 M to about 0.2 M. The growth of the gold nanorods is spectroscopically monitored during a period of anisotropic growth of the gold nanorods. The period of anisotropic growth is characterized by a red shift in a longitudinal surface plasmon resonance absorbance spectrum. A second growth solution is added to the gold nanorod synthesis mixture based on the monitoring of the growth at a time where the red shift in the longitudinal surface plasmon resonance absorbance spectrum ceases or begins a blue shift in the longitudinal surface plasmon resonance absorbance spectrum. The second growth solution includes the initial gold precursor and the reducing agent in the initial surfactant solution.

A variety of options are available for the second aspect of the invention. The gold seed crystals may be formed prior to introducing the gold seed crystals into the initial growth solution by reacting a solution of sodium borohydride with a solution comprising a preliminary gold precursor in a preliminary surfactant solution comprising a cetyl trimethyl ammonium surfactant having a concentration range of about 0.05 M to about 0.2 M. The gold seed crystals may be aged for a duration of about 1 minute to about 15 minutes prior to introducing the gold seed crystals into the initial growth solution. The initial or the preliminary gold precursor may comprise HAuCl4 or any other gold (III) halide including gold (III) bromide, gold(III) iodide, gold(III) fluoride or hydrated gold(III) halide, or combinations thereof. The cetyl trimethyl ammonium surfactant may comprise a cetyl trimethyl ammonium surfactant solution or any other quarternary ammonium bromide surfactant or combination of quaternary ammonium bromide surfactant and quaternary ammonium halide surfactant. The initial gold precursor may be present in the initial growth solution in a sufficient quantity to provide an initial gold precursor concentration of at least about 0.25 mmol/L. The initial gold precursor concentration may be in a range greater than 0.25 mmol/L to less than about 0.05 mol/L. The additional gold precursor may be present in the second growth solution in a sufficient quantity to provide an additional gold precursor concentration of about 0.25 mmol/L or more. The additional gold precursor concentration may be in a range greater than 0.25 mmol/L to less than about 0.05 mol/L.

In a further aspect, a method for synthesizing gold nanorods includes the steps of reacting a solution of sodium borohydride with a solution having a preliminary gold precursor in a preliminary surfactant solution provided by a surfactant having a concentration range of about 0.05 M to about 0.2 M to provide gold seed crystals. The gold seed crystals are introduced into an initial growth solution to form a gold nanorod synthesis mixture. The initial growth solution includes an initial gold precursor and a reducing agent in an initial surfactant solution provided by a cetyl trimethyl ammonium surfactant having a concentration range of about 0.05 M to about 0.2 M. Growth of the gold nanorods is spectroscopically monitored during a period of anisotropic growth of the gold nanorods. The period of anisotropic growth is characterized by a red shift in a longitudinal surface plasmon resonance absorbance spectrum. A second growth solution is added to the gold nanorod synthesis mixture based on the monitoring of the growth at a time where the red shift in the longitudinal surface plasmon resonance absorbance spectrum ceases or begins a blue shift in the longitudinal surface plasmon resonance absorbance spectrum. The second growth solution includes the initial gold precursor and the reducing agent in the initial surfactant solution.

A variety of options are available for the third aspect of the invention. The gold seed crystals may be aged for a duration of about 1 minute to about 15 minutes prior to introducing the gold seed crystals into the initial growth solution. The initial or the preliminary gold precursor may comprise $HAuCl_4$ or any other gold (III) halide including gold (III) bromide, gold(III) iodide, gold(III) fluoride or hydrated gold (III) halide, or combinations thereof. The surfactant may comprise a cetyl trimethyl ammonium surfactant or a quarternary ammonium bromide surfactant or a combination of a quaternary ammonium bromide surfactant and a quaternary ammonium halide surfactant.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein:

FIG. 1 shows examples of synthesis of nanostructures according to the invention.

DETAILED DESCRIPTION OF THE INVENTION

With initial reference to FIG. 1, examples of processes for the synthesis of nanostructures according to the invention are shown. The invention is described in connection with examples for the synthesis of gold nanostructures, and, in particular, gold nanorods. The invention may be utilized to make other nanostructures besides nanorods, and utilizing materials other than gold. The methods of the invention may be utilized to make various nanostructures from various starting materials.

The left-hand column of FIG. 1 depicts general aspects of a process for synthesis of gold nanostructures according to the disclosure. The right-hand column of FIG. 1 depicts a specific example of a process for synthesis of gold nanostructures according to the disclosure. The specific example is described in more detail below.

The methods involve introducing a seed solution S of seed crystals into an initial growth solution $G_1$. The initial growth solution $G_1$ is made up of a precursor material and a reducing agent in a surfactant solution. The solution S of seed crystals and the initial growth solution $G_1$ form a nanostructure synthesis mixture in which growth of nanostructures is initiated.

Figure 2:
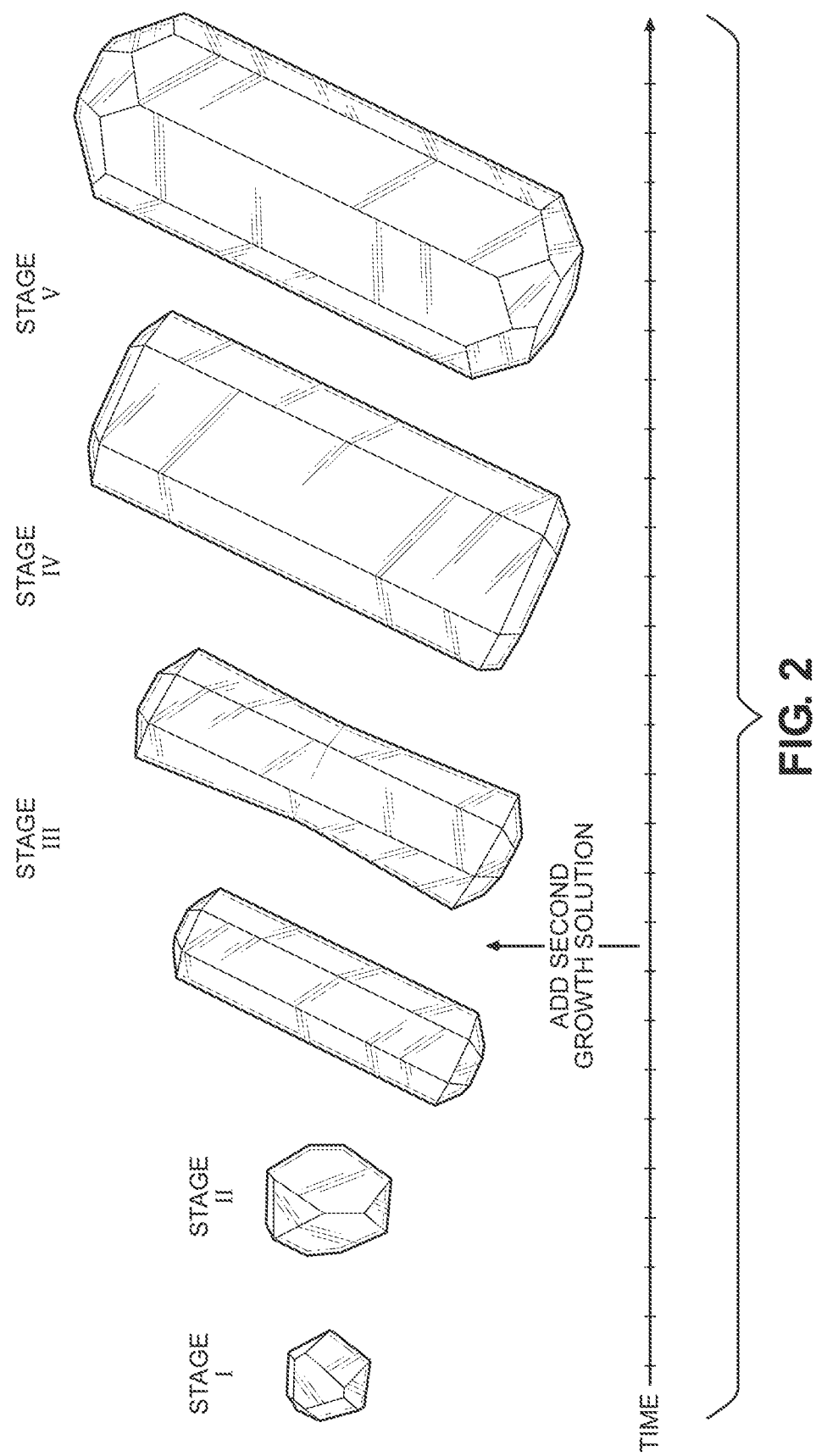
FIG. 2 illustrates growth phases of nanostructures and depicts identification of a specified time to add second growth solution in accordance with the invention.

Growth stages of the nanostructures are depicted in FIG. 2. In this regard, an aspect of the process involves the addition of a second growth solution $G_2$ to the nanostructure synthesis mixture at a determined time during the growth of the nanostructures. Accurate monitoring of the growth of the nanostructures is important to the production of the desired nanostructures.

The growth of nanostructures in the nanostructure synthesis mixture is monitored during a period of anisotropic growth of the nanostructures. The monitoring is conducted to determine a shift from stage II growth of the nanostructures to stage III growth of the nanostructures. When the shift from stage II growth to stage III growth is determined from the monitoring, the second growth solution $G_2$ is added to the nanostructure synthesis mixture.

The composition of the second growth solution $G_2$ is also important. In a preferred embodiment, the second growth solution $G_2$ includes more of the precursor material and the reducing agent of the surfactant solution of the initial growth solution $G_1$.

The process, by adding the second growth solution $G_2$ at the specified time as shown in FIG. 2, has been observed to result in acceleration of the growth of nanostructures as compared to conventional processes. By accelerating growth, improved yields and reduced nanostructure costs may be achieved.

For the purpose of example, as shown in the right-hand column of FIG. 1, the seed solution S is preferably provided by first introducing the precursor gold material into the initial growth solution $G_1$ by reacting a solution of sodium borohydride with a solution having a preliminary gold precursor in a preliminary surfactant solution including a cetyl trimethyl ammonium surfactant having a concentration range of about 0.05 M to about 0.2 M.

The seed solution S is preferably aged for a duration of about 1 minute to about 15 minutes, most preferably about 5 minutes prior to introducing the seed solution into the initial growth solution $G_1$.

The initial growth solution $G_1$ includes a precursor material and a reducing agent, preferably a mild reducing agent, in a surfactant solution. The surfactant solution is preferably water based.

In a preferred embodiment for the synthesis of gold nanostructures, as shown in the right-hand column of FIG. 1, the precursor material is $HAuCl_4$ or any other gold (III) halide including gold (III) bromide, gold(III) iodide, gold (III) fluoride or hydrated gold(III) halide, or combinations thereof. Preferred surfactants include a cetyl trimethyl ammonium surfactant solution or any other quarternary ammonium bromide surfactant or combination of quaternary ammonium bromide surfactant and quaternary ammonium halide surfactant. A preferred reducing agent is ascorbic acid, with the formula $C_6H_8O_6$. As noted above, the solvent is preferably water.

The seed solution S and the initial growth solution $G_1$ are preferably provided in relative amounts of from about $1S/1G_1$ to about $100S/100G_1$. After the shift from stage II growth to stage III growth is observed, the second growth solution $G_2$ is added, at a concentration of from about 1 $G_2$ to about 100 $G_2$.

It will be appreciated that the leading numbers, e.g. 1S, 20S, 1G1, 100G1, are scale up factors. For example, for the seed solution S, the number of seeds in the initial growth solution G1 is varied by changing the volume ratio of seed solution S to the initial growth solution G1. For example, if the volume of seed solution is increased from 10 µL to 5 mL per 10 mL reaction volume, this corresponds to a seed concentration scale up factor from 1 to 500, referred as 1S to 500S. Likewise, if the reactant concentration of the initial growth solution $G_1$ is increased by a factor of 10, this is referred as 1G1 to 10G1. This is likewise the case for the second growth solution G2. As such, in exemplary embodiments such as those in FIG. 1, when the concentration of the Au-precursor is increased by a factor of 10, the concentration of other reactants is increased by a factor of 10 so that the total reactant concentration is increased by a factor of 10 and the ratio between reactants remains fixed.

In accordance with the invention, the growth of the nanostructures in the nanostructure synthesis mixture is monitored during a period of anisotropic growth of the nanostructures to determine a shift from stage II growth of the nanostructures to stage III growth of the nanostructures, as explained below.

A significant aspect of the invention relates to monitoring the growth of the nanostructures to enable addition of the second growth solution at a specified time during the growth of the nanostructures. With continuing reference to FIG. 1 and as depicted in FIG. 2, after the shift from stage II growth to stage III growth is identified, e.g., such as by spectroscopic monitoring, the second growth solution $G_2$ is introduced to the nanostructure synthesis mixture. The second growth solution $G_2$ includes the precursor material and the reducing agent in the surfactant solution.

With continuing reference to FIG. 2, growth phases of nanostructures, and in particular gold nanorods, are depicted as a function of time. Characteristics of the stages of nanostructure growth are discussed in detail below. Nanostructure growth stage characteristics are well known in the art. The time indicated by the arrow for adding the second growth solution corresponds to the shift from stage II growth to stage III growth.

Stage I nanostructure growth is characterized by rapid isotropic growth, where seed particles form with a mixture of {100} and {111} Miller Index facets and isotropically grow to spherical nanoparticles having about 6 nm diameter.

Stage II nanostructure growth is characterized by rapid anisotropic growth, where particles grow in one direction, substantially retaining the diameter of the initial spherical particle, and form a spherocylinder. The growth rate of the rod length is significantly faster than that of the diameter.

Stage III nanostructure growth is characterized by a fast, non-uniform rod growth, where the growth rate of the rod length has gradually decreased while the growth rate of the diameter becomes slightly faster. Around the rod end, the growth rate of the diameter becomes faster than the length causing a lateral flaring of the rod leading to a dumbbell shape.

Stage IV nanostructure growth is characterized by side facets reconstruction, where the overall growth significantly slows down. The growth rate of both the length and the diameter decreases. The rod sides become more even and the hemispherical ends of the rods become noticeably flattened.

Finally, Stage V nanostructure growth is characterized by relaxation, where the shape of the rod end recuperates its hemispherical shape and evolves toward a thermodynamically stable shape. In this stage, there is a minuscule decrease in the length and a progressive increase in the diameter. The growth rate is insignificant.

In a preferred embodiment, monitoring of the growth of the nanostructures is done by spectroscopic monitoring. The determination of a shift from stage II growth of the nanostructures to stage III growth of the nanostructures includes determining a period of anisotropic growth characterized by a cessation of a red shift in the longitudinal surface plasmon resonance absorbance spectrum or a beginning of a blue shift in the longitudinal surface plasmon resonance absorbance spectrum.

Figure 3:
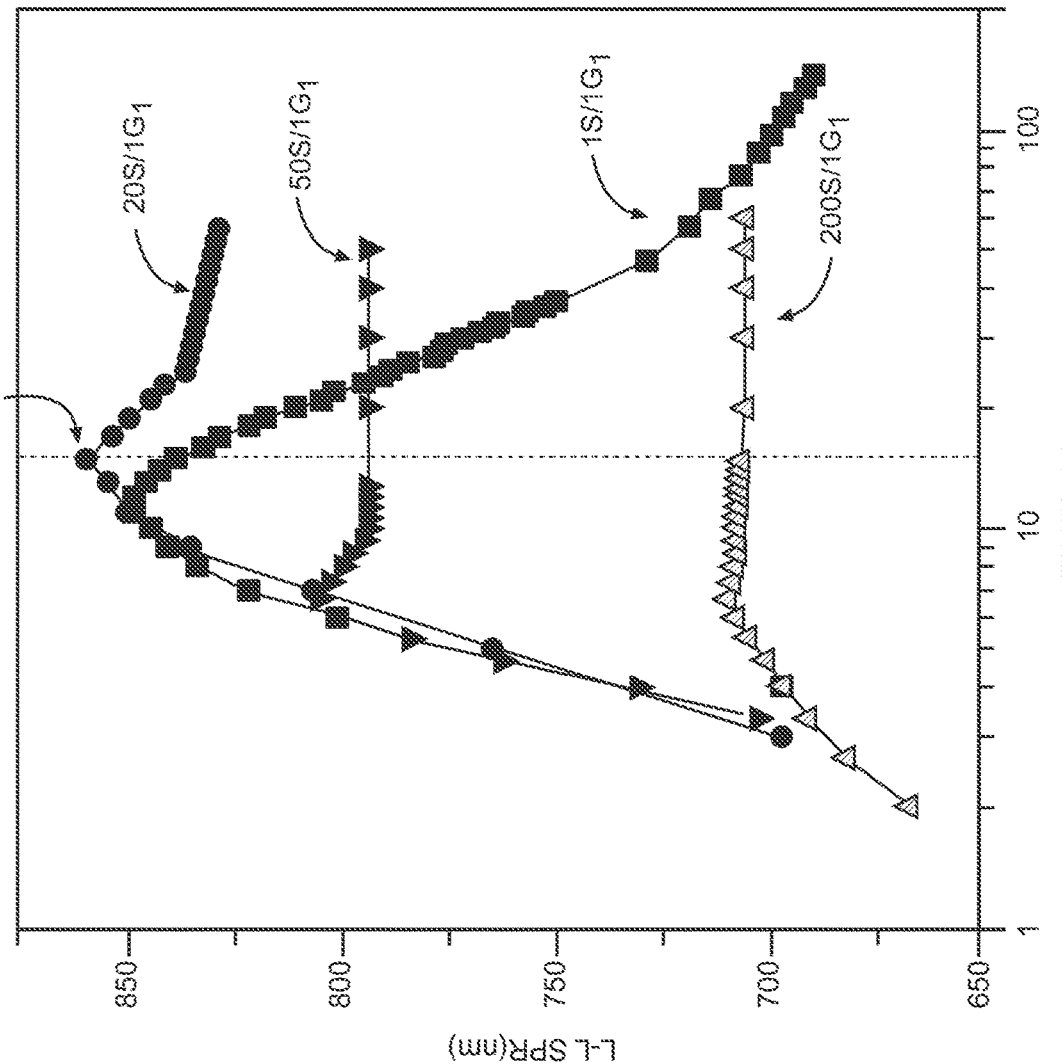
FIG. 3 shows, for various seed and initial growth solution concentrations, the longitudinal surface plasmon resonance absorbance spectrum (L-LSPR) versus time corresponding to nanostructure growth.

FIG. 3 depicts growth rates observed for seed solutions S and initial growth solutions $G_1$ mixtures having concentrations of $1S/1G_1$, $2S/1G_1$, $50S/1G_1$, and $200S/1G_1$ versus time. The time indicated by the dashed vertical line generally corresponds to the shift from stage II growth to stage III growth for the $20S/1G_1$ data, and the specified time for adding the second growth solution $G_2$, as depicted in FIG. 3. The change in the plasmon peak is monitored by spectroscopic monitoring. The change in the peak is indicative of the aspect ratio of the nanostructures, and indicates a shift from stage II growth of the nanostructures to stage III growth. Aspect ratio is the ratio of the width to the length of the nanostructure, in this case, a nanorod. The second growth solution $G_2$ was not added in the growth represented in FIG. 3.

As will be noted, the time of the shift varies depending upon concentration of the seed solution S in the initial growth solution $G_1$. For example, as the concentration of the seed solution increases, the onset of the shift from stage II to stage III growth generally begins earlier as will be observed from the peaks shown in FIG. 3. It will be appreciated that an increase in temperature of the growing conditions also will speed up the timing of the growth stages. Preferably, the temperature is between about 25-30 C. Thus, it is very important to monitor the growth as described herein so that the change in the peak can be detected, which signals the time to add the second growth solution $G_2$.

As will be observed, the maximum anisotropic growth is possible for the concentration combination of seed solution S and initial growth solution $G_1$ from 20S/1G1 to $50S/1G_1$. As seen, the anisotropic growth for the $200S/1G_1$ mixture was the lowest observed. Thus, it is preferred to utilize concentrations greater than $1S/1G_1$, and less than $100S/1G_1$, most preferably from $20S/1G_1$ to $50S/1G_1$. The notation $nS/mG_1$ will be understood as n times higher concentration of seed solution S is added to m times higher concentration of initial growth solution G1.

As noted, the second growth solution $G_2$ is added after the shift from stage II growth to stage III growth is identified. The second growth solution includes the precursor material and the reducing agent in the surfactant solution of the initial growth solution and is preferably provided in an amount of from about $1G_2$ up to about $100G_2$.

Figure 4:
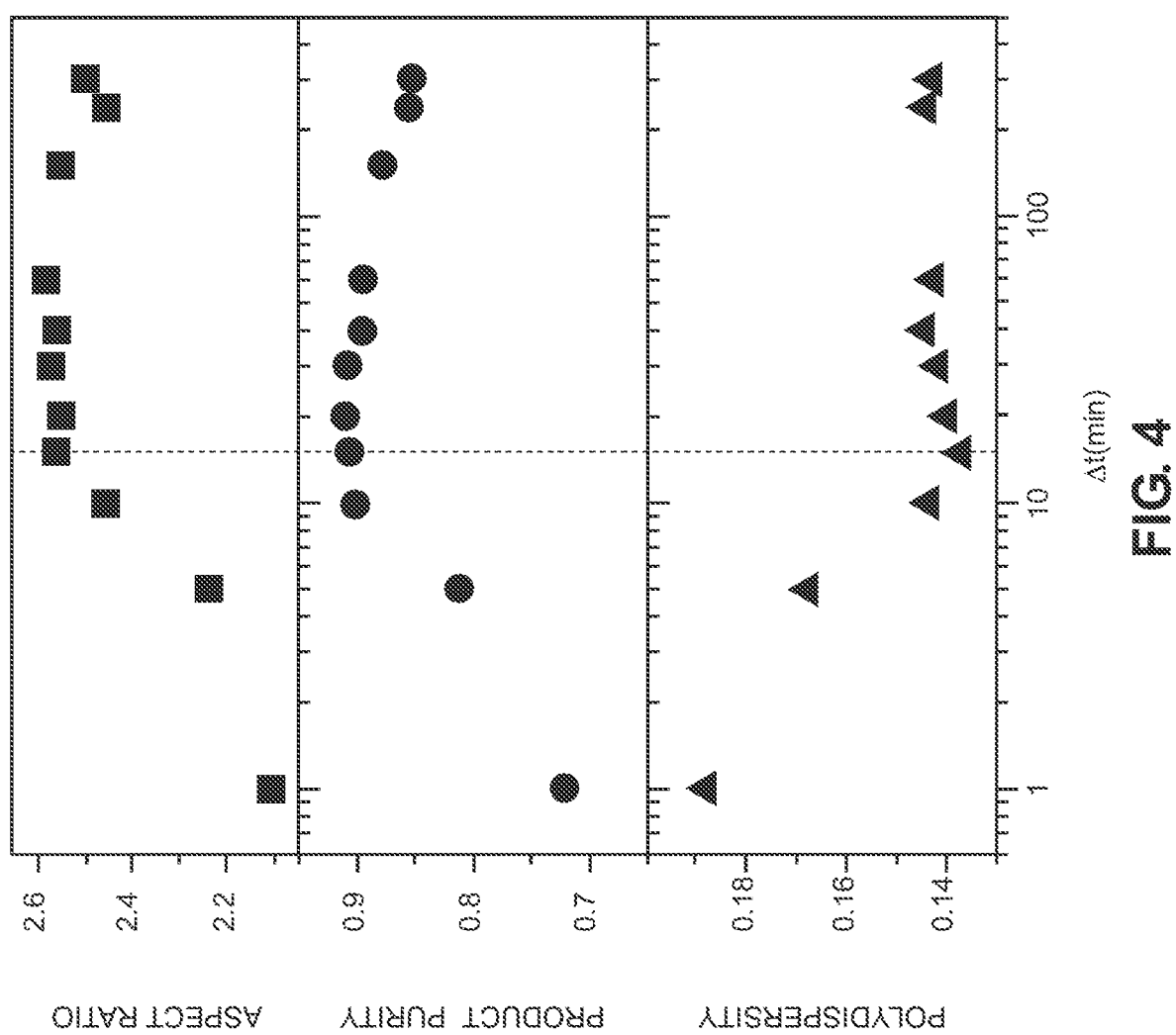
FIG. 4 shows growth characteristics of nanostructures versus time.

FIG. 4 shows growth characteristics of nanostructure growth versus time for gold nanorods grown from a seed solution S and initial growth solution $G_1$ synthesis mixture of 20S/1G1, followed by addition of a second growth solution $G_2$ in a concentration of $20G_2$. The second growth solution $G_2$ was added to the $20S/1G_1$ mixture at the time shown in FIG. 3 for the $20S/1G_1$ nanostructure synthesis mixture. As previously noted, the time indicated by the dashed vertical line corresponds to the shift from stage II growth to stage III growth, which is the specified time when the second growth solution $G_2$ is introduced. As will be observed, the addition of the concentrated second growth solution $G_2$ at the specified time, which is coincident with the shift from stage II growth to stage III growth, serves to advantageously accelerate the growth of the nanostructures. The addition of second growth solution $G_2$ within about 5 minutes of identification of the shift from stage II growth to stage III growth is considered to be coincident with the shift and will result in optimal quality of the gold nanorods produced. The results correspond to enhanced product quality (polydispersity to aspect ratio) and product purity.

It has been observed that addition of the second growth solution $G_2$ at times other than as specified herein have undesirable results. For example, addition of $20G_2$ solution during stage I and early stage II of the first growth step (t1<15 min) was observed to significantly disturb the initial anisotropic growth. This deteriorated the product purity and the product quality. Also, using longer times for the first growth step (t1>30 min) also deteriorated product quality, decreasing product purity and rod quality. Overall, the highest aspect ratio and the least impurities, and narrowest polydispersity, for this 20S/1G+20G2 example occurred when the second growth solution $G_2$ was added at the end of stage II growth (t1≈15 and 30 min), as described herein and shown in FIG. 4.

Methods according to the disclosure advantageously enable enhanced synthesis of nanostructures, characterized by substantially increased growth rates of nanostructures resulting from the targeted addition of a second and preferably concentrated growth solution after identifying the shift from stage II growth to stage III growth. The increased growth rates provide increased yield of nanostructures, which is advantageous to reduce costs of the production of nanostructures.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A method comprising:
   introducing a solution of gold seed crystals into an initial growth solution to form a nanostructure synthesis mixture, wherein the initial growth solution comprises an initial precursor material comprising gold and an initial reducing agent in a surfactant solution;
   identifying, based upon growth of nanostructures in the nanostructure synthesis mixture during a period of anisotropic growth of the nanostructures, a shift from stage II growth of the nanostructures to stage III growth of the nanostructures; and
   after identifying the shift, introducing a second growth solution to the nanostructure synthesis mixture coincident in time with the shift, wherein the second growth solution comprises an additional precursor material and an additional reducing agent in the surfactant solution.

2. The method of claim 1 further comprising monitoring the growth of the nanostructures using spectroscopic monitoring to identify the shift from stage II growth of the nanostructures to stage III growth of the nanostructures.

3. The method of claim 1 further comprising aging the nanostructure synthesis mixture until the nanostructures comprise nanorods.

4. The method of claim 1, wherein the surfactant solution has a concentration of from 0.05 M to 0.2 M.

5. The method of claim 1, wherein the surfactant solution comprises a cetyl trimethyl ammonium surfactant solution or any other quaternary ammonium bromide surfactant or a combination of a quaternary ammonium bromide surfactant and a quaternary ammonium halide surfactant.

6. The method of claim 1 further comprising monitoring the growth of the nanostructures using spectroscopic monitoring, identifying a shift from stage II growth of the nanostructures to stage III growth of the nanostructures comprises determining a period of anisotropic growth characterized by a cessation of a red shift in a longitudinal surface plasmon resonance absorbance spectrum or a beginning of a blue shift in the longitudinal surface plasmon resonance absorbance spectrum.

7. A method for synthesizing gold nanorods, comprising:
   introducing gold seed crystals into an initial growth solution to form a gold nanorod synthesis mixture, wherein the initial growth solution comprises an initial precursor comprising gold, and an initial reducing agent in an initial surfactant solution comprising a cetyl trimethyl ammonium surfactant having a concentration range of 0.05 M to 0.2 M;
   spectroscopically monitoring growth of the gold nanorods during a period of anisotropic growth of the gold nanorods, wherein the period of anisotropic growth is characterized by a red shift in a longitudinal surface plasmon resonance absorbance spectrum; and
   adding a second growth solution to the gold nanorod synthesis mixture based on the monitoring of the growth at a time where the red shift in the longitudinal surface plasmon resonance absorbance spectrum ceases or begins a blue shift in the longitudinal surface plasmon resonance absorbance spectrum, wherein the second growth solution comprises an additional precursor comprising gold and an additional reducing agent in the initial surfactant solution.

8. The method of claim 7, wherein the gold seed crystals are formed prior to introducing the gold seed crystals into the initial growth solution by reacting a solution of sodium borohydride with a solution comprising a preliminary precursor comprising gold in a preliminary surfactant solution comprising a cetyl trimethyl ammonium surfactant having a concentration range of 0.05 M to 0.2 M.

9. The method of claim 8, wherein the gold seed crystals are aged for up to 15 minutes prior to introducing the gold seed crystals into the initial growth solution.

10. The method of claim 7, wherein the initial or the preliminary precursor comprises $HAuCl_4$ or any other gold (III) halide including gold (III) bromide, gold (III) iodide, gold (III) fluoride or hydrated gold(III) halide, or combinations thereof.

11. The method of claim 7, wherein the cetyl trimethyl ammonium surfactant comprises a cetyl trimethyl ammonium surfactant solution or any other quaternary ammonium bromide surfactant or combination of quaternary ammonium bromide surfactant and quaternary ammonium halide surfactant.

12. The method of claim 7, wherein the initial precursor is present in the initial growth solution in a sufficient quantity to provide an initial precursor concentration of at least 0.25 mmol/L.

13. The method of claim 12, wherein the initial precursor concentration is in a range greater than 0.25 mmol/L to less than 0.05 mol/L.

14. The method of claim 7, wherein the additional precursor is present in the second growth solution in a sufficient quantity to provide an additional precursor concentration of 0.25 mmol/L or more.

15. The method of claim 13, wherein the additional precursor concentration is in a range greater than 0.25 mmol/L to less than 0.05 mol/L.

16. A method for synthesizing gold nanorods, comprising:
reacting a solution of sodium borohydride with a solution comprising a preliminary precursor comprising gold in a preliminary surfactant solution comprising a surfactant having a concentration range of 0.05 M to 0.2 M to provide gold seed crystals;
introducing the gold seed crystals into an initial growth solution to form a gold nanorod synthesis mixture, wherein the initial growth solution comprises an initial precursor comprising gold and a reducing agent in an initial surfactant solution comprising a cetyl trimethyl ammonium surfactant having a concentration range of 0.05 M to 0.2 M; and
adding a second growth solution to the gold nanorod synthesis mixture based on a time where rapid anisotropic growth of nanostructures in the gold nanorod synthesis mixture changes to non-uniform rod growth, wherein the second growth solution comprises an additional precursor comprising gold and the reducing agent in the initial surfactant solution.

17. The method of claim 16, wherein the gold seed crystals are aged for a duration of 1 minute to 15 minutes prior to introducing the gold seed crystals into the initial growth solution.

18. The method of claim 16, wherein the initial or the preliminary precursor comprises $HAuCl_4$ or any other gold (III) halide including gold (III) bromide, gold(III) iodide, gold(III) fluoride or hydrated gold (III) halide, or combinations thereof.

19. The method of claim 16, wherein the surfactant comprises a cetyl trimethyl ammonium surfactant or a quaternary ammonium bromide surfactant or a combination of a quaternary ammonium bromide surfactant and a quaternary ammonium halide surfactant.

* * * * *